US008658765B2

(12) United States Patent
Martin, Jr. et al.

(10) Patent No.: US 8,658,765 B2
(45) **Date of Patent: *Feb. 25, 2014**

(54) NON-NATURAL MIC PROTEINS

(75) Inventors: David W. Martin, Jr., Mill Valley, CA (US); Steven R. Williams, San Francisco, CA (US)

(73) Assignee: AvidBiotics Corp., South San Francisco, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 12/982,827

(22) Filed: Dec. 30, 2010

(65) Prior Publication Data

US 2011/0183893 A1 Jul. 28, 2011

Related U.S. Application Data

(60) Provisional application No. 61/291,749, filed on Dec. 31, 2009.

(51) Int. Cl.

| | |
|---|---|
| *A61K 38/16* | (2006.01) |
| *C07K 14/00* | (2006.01) |
| *C07K 16/00* | (2006.01) |
| *A01N 63/00* | (2006.01) |

(52) U.S. Cl.
USPC ......................... 530/345; 530/350; 530/387.1

(58) Field of Classification Search
None
See application file for complete search history.

(56) References Cited

U.S. PATENT DOCUMENTS

| | | | |
|---|---|---|---|
| RE39,789 E | 8/2007 | Raulet et al. | |
| 7,771,718 B2 | 8/2010 | Spies et al. | |
| 2009/0226466 A1 | 9/2009 | Fong et al. | |
| 2011/0183893 A1 | 7/2011 | Martin, Jr. et al. | |
| 2011/0311561 A1 | 12/2011 | Martin, Jr. et al. | |

FOREIGN PATENT DOCUMENTS

| | | |
|---|---|---|
| WO | WO00/06605 | 2/2000 |
| WO | WO2005/052004 | 6/2005 |
| WO | WO2005/061547 | 7/2005 |
| WO | WO2006/024367 | 3/2006 |
| WO | WO2007/068354 | 6/2007 |
| WO | WO2007/097812 | 8/2007 |
| WO | WO2008/058728 | 5/2008 |

OTHER PUBLICATIONS

Rudikoff et al (Proc Natl Acad Sci USA 1982 vol. 79 p. 1979).*
Casset et al (2003 BBRC 307, 198-205).*
Groh, V., et al., "Tumour-Derived Soluble MIC Ligands Impair Expression of NKG2D and T-Cell Activation," Nature 419:734-8 (2002).
Vetter, CS., et al., "Loss of Nonclassical MHC Molecules MIC-A/B Expression During Progression of Uveal Melanoma," British Journal of Cancer 91:1495-9 (2004).
Weiner, L., et al., "Targeted Therapy," Fox Chase Cancer Center 2006 Scientific Report, Internet at .fccc.edu/docs/sci_report/Weiner.pdf.
Suck, G., et al., "Novel approaches using natural killer cells in cancer therapy" Seminars in Cancer Biology 16:412-418 (2006).
Steinle, A., et al., "Interactions of human NKG2D with its ligands MICA, MICB and homologs of the mouse RAE-1 protein family" Immunogenetics 53:279-287 (2001).
Koide, A., et al., "High affinity single-domain binding proteins with a binary-code interface" PNAS 104(16):6632-6637 (2007).
Jager, M., et al., "The trifunctional antibody ertumaxomad destroys tumor cells that express low levels of human epidermal growth factor receptor 2" Cancer Res 69(10):4270-4276 (2009).
Gasser, S., et al., "The DNA damage response, immunity and cancer" Seminars in cancer biology 16:344-347 (2006).
Diefenbach, A., et al., "Strategies for target cell recognition by natural killer cells", Immunological Reviews 181:170-184 (2001).
Coudert, J., et al., "The role of the NKG2D receptor for tumor immunity" Seminars in Cancer Biology 16:333-343 (2006).
Chang, C., et al.," NK cell activating ligands on human malignant cells: molecular and functional defects and potential clinical relevance" Seminars in Cancer Biology 16:383-392 (2006).
Bargou, R., et al., "Tumor Regression in Cancer Patient by Very Low Doses of a T Cell Engaging Antibody" Science 321: 974 (2008).
Uherek, C., et al., "Retargeting of natural killer-cell cytolytic activity to ErbB2-expressing cancer cells results in efficient and selective tumor cell destruction", Blood 10:1265-1273 (2002).
Friese, M. et al. "MICA/NKG2D-mediated immunogene therapy of experimental gliomas." Cancer Research 63: 8996-9006 (2003).
Fuertes, M., et al., Intracellular retention of the NKG2D ligand MHC class I chain related gene A in human melanomas confers immune privilege and prevents NK cell-mediated cytotoxocity: J Immunol 180:4606-4614 (2008).
Bahram, S, et al., "A second lineage of mammalian MHC class I genes" PNAS 91:6259-6263. (1994).
Busche, A et al. "Natural killer cell mediated rejection of experimental human lung cancer by genetic overexpression of MHC class I chain-related gene A." Human Gene Therapy 17: 135-146.(2006).
Germain, C., et al., "MHC Class I- related chain A conjugated to antitumor antibodies can sensitize tumor cells to specific lysis by natural killer cells" Clinical Cancer Res 11(20):7516-7522 (2005).
Guo, H et al. "Diversity-Generating Retroelement Homing Regenerates Target Sequences for Repeated Rounds of Codon Rewriting and Protein Diversification." Molecular Cell 31, 813-823. (2008).

(Continued)

*Primary Examiner* — G. R. Ewoldt
*Assistant Examiner* — Marianne Dibrino
(74) *Attorney, Agent, or Firm* — Sughrue Mion, PLLC

(57) ABSTRACT

This invention describes soluble, monovalent, non-natural protein molecules that can activate NK cells and certain T-cells to attack specific cellular target cells by attaching the NKG2D-binding portions of monovalent MICA or MICB protein, i.e. their α1-α2 platform domain, to the intended target cell specifically. The α1-α2 domain is contiguous with a heterologous α3 domain that has been genetically modified to bind directly or indirectly to the extracellular aspect of the target cell, thereby serving as the targeting domain. The genetic modification to create a non-natural and non-terminal targeting motif within the α3 domain can include a portion of an antibody, another protein molecule or portion thereof, a peptide, or a non-natural, modified α3 domain of a MIC protein.

13 Claims, 8 Drawing Sheets

(56) References Cited

OTHER PUBLICATIONS

Holmes, M.A, et al., "Structural Studies of Allelic Diversity of the MHC Class I Homolog MICB, a Stress-Inducible Ligand for the Activating Immunoreceptor NKG2D." J Immunol. 169: 1395-1400. (2001).

Li, P. et al.,"Crystal structure of the MHC class I homolog MICA, a yγT cell ligand." Immunity 10: 577-584 (1999).

GenBank Report Accession No. AAA2118, submitted 1994.

Robert, B., et al., "Antibody-conjugated MHC class I tetramers can target tumor cells for specific lysis by T lymphocytes." Eur J. Immunol. 30:3165-3170 (2000).

Ogg, G.S., et al., "Sensitization of tumour cells to lysis by virus-specific CTL using antibody-targeted MHC class I/peptide complexes" Br. J. Cancer 2000 82:1058-1062.

Lev, A., et al., "Recruitment of CTL activity by tumor-specific antibody-mediated targeting of single-chain class IMHC-peptide complexes" J. Immunol. 2002 169:2988-2996.

Lev, A., et al., "Tumor specific Ab-mediated targeting fMHC-peptide complexes induces regression of human tumor xenografts in vivo" Proc Natl Acad Sci USA 2004 14:3-11.

Donda, A., et al., "in vivo targeting of an anti-tumor antibody coupled to antigenic MHC class I complexes induces specific growth inhibition and regression of established syngeneic tumor grafts" Cancer Immun. 2003 14:3-11.

Bahram, S., et al. "Nucleotide sequence of human MHC class I MICB cDNA." Immunogenetics 43: 230-233 (1996).

Bauer, et al., "Activation of NK cells and T cells by NKG2D, a receptor for stress-inducible MICA." Science 285: 727-730 (1999).

Groh V, et al., "Co-stimulation of CD8+ aβT-cells by NKG2D via engagement by MIC induced on virus-infected cells." Nat. Immunol. 2: 255-260. (2001).

Li, P. et al.,"Complex structure of the activating immunoreceptor NKG2D and its MHC class I-like ligand MICA." Nature Immunol. 2: 443-451(2001).

Stephens, H.A., "MICA and MICB genes: can the enigma of their polymorphism be resolved?" Trends Immunol. 22: 378-85 (2001).

Robert, B., et al., "Redirecting anti-viral CTL against cancer cells by surface targeting of monomeric MHC Class I-viral peptide coupled to antibody fragments" Cancer Immun. 1:2 (2001).

Bahram, S., et al. "Nucleotide sequence of the human MHC class I MICA gene." Immunogenetics 44:80-81 (1996a).

Martin, D.W.: "Targeted soluble MICA molecules to recurit innate immunity cells to kill specific. Project No. 1R43A1088979-01", Internet, Mar. 15, 2010, XP002662441, Retrieved from the Internet: URL:://projectreporter.nih.gov/project_info_details. cfm?aid=7907360&icde=0 [retrieved on Oct. 27, 2011] the whole document.

Martin, D.W.: "Targeted soluble MICA molecules to recurit innate immunity cells to kill specific. Project No. 1R43AI088979-01", Internet, Mar. 15, 2010, XP002662441, Retrieved from the Internet: URL:http://projectreporter.nih.gov/project_info_details. cfm?aid=7907360&icde=0 [retrieved on Oct. 27, 2011] the whole document.

Zwirner, N.W., et al., "Immunobiology of the human MHC class I chain-related gene A (MICA): From transplantation immunology to tumor immune escape", Immunologia vol. 25, No. 1, Jan. 1, 2006, pp. 25-38.

Gong W.J., et al., [Effects of recombinant soluble MICA protein on the biologic activities of NK cells]. Xi Bao Yu Fen Zi Mian Yi Xue Za Zhi = Chinese Journal of Cellular and Molecular Immunology Oct. 2009 LNKD—Pubmed: 19811738, vol. 25, No. 10, Oct. 2009, pp. 903-906, abstract.

Marten, A., et al., "Inhibition of cytotoxic gamma/ delta T cells by pancreatic carcinoma patients' derived soluble MIC+ serum could be restored by capturing soluble MIC with antibodies", Gastroenterology vol. 128, No. 4, Suppl. 2, Apr. 1, 2005, p. A532, T1699.

Robinson, J., et al., "MICA sequences 2000", Immunogenetics vol. 53, No. 2, Mar. 1, 2001, pp. 150-169.

Stern-Ginossar, et al., "Host immune system gene targeting by viral miRNA." Science 317:376-381 (2007).

Touze, T., et al., "Self-association of EPEC intimin mediated by the beta-barrel-containing anchor domain: a role in clustering of the Tir receptor." Mol Microbiol. 51:73-87 (2004).

Weis, et al., "The C-type lectin superfamily in the immune system." Immunol. Rev. 163:19-34. (1998).

Wentzel, A., et al., "Display of passenger proteins on the surface of Escherichia coli K-12 by the enterohemorrhagic E. coli intimin EaeA." J Bacteriol. 183:7273-84 (2001).

Zwirner, et al., "Differential expression of MICA by endothelial cells, fibroblasts, keratinocytes and monocytes." Human Immunol. 60: 323-330 (1999).

Stern-Ginossar, et al., "Human MicroRNAs regulate stress-induced immune responses mediated by the receptor NKG2D." Nature Immunol. 9:1065-1073 (2008).

* cited by examiner

Figure 1.

Figure 2. A DGR-based approach for diversifying the α3 domain of human MIC-A.

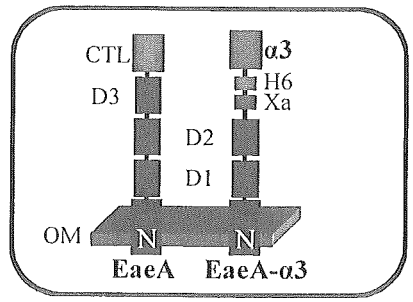
Figure 3. Structures of EaeA an the EaeA-α3 fusion proteins displayed on the surface of E. coli. OM is outer membrane, D1-D3 are Ig superfamily motifs, Xa is a factor X cleavage site, and H6 is hexa-histidine.
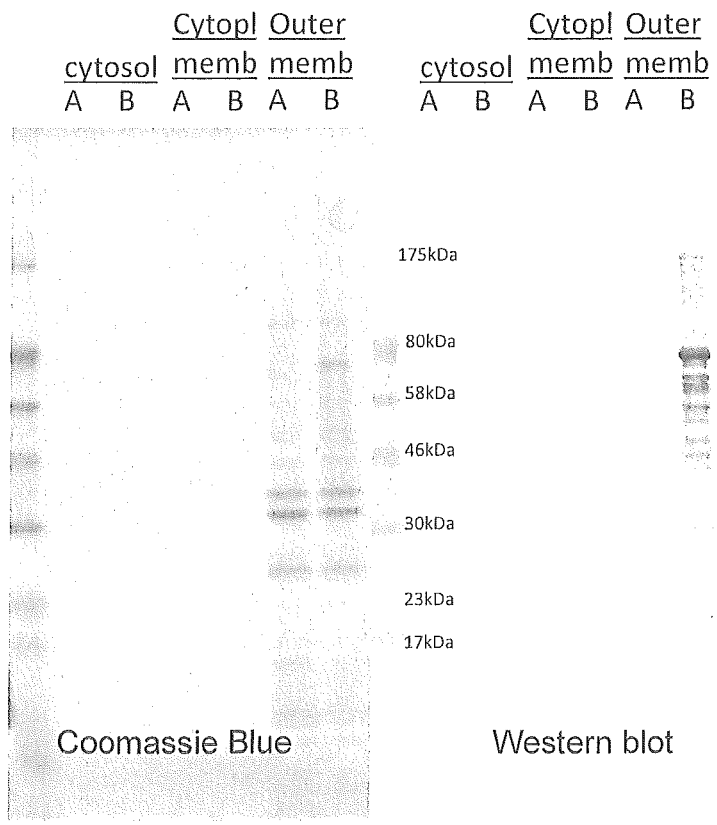
Figure 4:

SEQ. ID. NO. 1 MICA
      1 ephslrynlt vlswdgsvqs gfltevhldg qpflrcdrqk crakpqgqwa edvlgnktwd
     61 retrdltgng kdlrmtlahi kdqkeglhsl qeirvceihe dnstrssqhf yydgelflsq
    121 nleteewtmp qssraqtlam nvrnflkeda mktktlyham hadclqelrr ylksgvvlrr
    181 tvppmvnvtr seasegnitv tcrasgfypw nitlswrqdg vslshdtqqw gdvlpdgnct
    241 yqtwvatric qgeeqrftcy mehsgnhsth pvps SEQ. ID. NO. 2 MICA
      1 ephslrynlt vlswdgsvqs gflaevhldg qpflrcdrqk crakpqgqwa edvlgnktwd
     61 retrdltgng kdlrmtlahi kdqkeglhsl qeirvceihe dnstrssqhf yydgelflsq
    121 nleteewtmp qssraqtlam nirnflkeda mktkthyham hadclqelrr ylksgvvlrr
    181 tvppmvnvtr seasegnitv tcrasgfypw nitlswrqdg vslshdtqqw gdvlpdgnct
    241 yqtwvatric qgeeqrftcy mehsgnhsth pvps SEQ. ID. NO. 3 MICA
      1 ephslpynlt vlswdgsvqs gflaevhldg qpflrydrqk crakpqgqwa edvlgnktwd
     61 retrdltgng kdlrmtlahi kdqkeglhsl qeirvceihe dnstrssqhf yydgelflsq
    121 nleteewtmp qssraqtlam nvrnflkeda mktkthyham hadclqelrr ylksgvvlrr
    181 tvppmvnvtr seasegnitv tcrasgfypw nitlswrqdg vslshdtqqw gdvlpdgnct
    241 yqtwvatric qgeeqrftcy mehsgnhsth pvps SEQ. ID. NO. 4 MICA
      1 ephslrynlt vlswdgsvqs gflaevhldg qpflrydrqk crakpqgqwa edvlgnktwd
     61 retrdltgng kdlrmtlahi kdqkeglhsl qeirvceihe dnstrssqhf yydgelflsq
    121 nleteewtvp qssraqtlam nvrnflkeda mktkthyham hadclqelrr ylesgvvlrr
    181 tvppmvnvtr seasegnitv tcrassfypr nitltwrqdg vslshdtqqw gdvlpdgnct
    241 yqtwvatric qgeeqrftcy mehsgnhsth pvps SEQ. ID. NO. 5 MICA
      1 ephslrynlt vlswdgsvqs gfltevhldg qpflrcdrqk crakpqgqwa edvlgnktwd
     61 retrdltgng kdlrmtlahi kdqkeglhsl qeirvceihe dnstrssqhf yydgelflsq
    121 nleteewtmp qssraqtlam nvrnflkeda mktkthyham hadclqelrr ylksgvvlrr
    181 tvppmvnvtr seasegnitv tcrasgfypw nitlswrqdg vslshdtqqw gdvlpdgnct
    241 yqtwvatric qgeeqrftcy mehsgnhsth pvps SEQ. ID. NO. 6 MICA
      1 ephslrynlt vlswdgsvqs gflaevhldg qpflrcdrqk crakpqgqwa edvlgnktwd
     61 retrdltgng kdlrmtlahi kdqkeglhsl qeirvceihe dnstrssqhf yydgelflsq
    121 nleteewtmp qssraqtlam nvrnflkeda mktkthyham hadclqelrr ylksgvvlrr
    181 tvppmvnvtr seasegnitv tcrasgfypw nitlswrqdg vslshdtqqw gdvlpdgnct
    241 yqtwvatric qgeeqrftcy mehsgnhsth pvps

FIGURE 6A

SEQ. ID. NO. 7 MICB
```
  1 phslrynlmv lsqdgsvqsg flaeghldgq pflrydrqkr rakpqgqwae dvlgaktwdt
 61 etedltengq dlrrtlthik dqkgglhslq eirvceihed sstrgsrhfy ydgelflsqn
121 letqestvpq ssraqtlamn vtnfwkedam ktkthyramq adclqklqlp pmvnvicsev
181 seqnitvtcr assfyprnit ltwrqdgvsl shntqqwgdv lpdgngtyqt wvatrirqge
241 eqrftcymeh sgnhgthpvp sgkalvlqsq rtdfpyvsaa mpcfviiiil cvpcckkkts
301 aaegp
```

SEQ. ID. NO. 8 MICB
```
  1 phslrynlmv lsqdgsvqsg flaeghldgq pflrydrqkr rakpqgqwae dvlgaetwdt
 61 etedltengq dlrrtlthik dqkgglhslq eirvcemhed sstrgsrhfy yngelflsqn
121 letqestvpq ssraqtlamn vtnfwkedam ktkthyramq adclqklqry lksgvairrt
181 vppmvnvtcs evseqnitvt crassfyprn itltwrqdgv slshntqqwg dvlpdgngty
241 qtwvatrirq geeqrftcym ehsgnhgthp vpsgkalvlq sqrtdfpyvs aampcfviii
301 ilcvpcckkk tsaaegp
```

SEQ. ID. NO. 9 MICB
```
  1 phslrynlmv lsqdgsvqsg flaeghldgq pflrydrqkr rakpqgqwae dvlgaktwdt
 61 etedltengq dlrrtlthik dqkgglhslq eirvceihed sstrgsrhfy ydgelflsqn
121 letqestvpq ssraqtlamn vtnfwkedam ktkthyramq adclqklqry lksgvairrt
181 vppmvnvics evseqnitvt crassfyprn itltwrqdgv slshntqqwg dvlpdgngty
241 qtwvatrirq geeqrftcym ehsgnhgthp vpsgkalvlq sqrtdfpyvs aampcfviii
301 ilcvpcckkk tsaaegp
```

SEQ. ID. NO. 10 MICB
```
  1 phslrynlmv lsqdgsvqsg flaeghldgq pflrydrqkr rakpqgqwae nvlgaktwdt
 61 etedltengq dlrrtlthik dqkgglhslq eirvceihed sstrgsrhfy ydgelflsqn
121 letqestvpq ssraqtlamn vtnfwkedam ktkthyramq adclqklqry lksgvairrt
181 vppmvnvtcs evseqnitvt crassfyprn itltwrqdgv slshntqqwg dvlpdgngty
241 qtwvatrirq geeqrftcym ehsgnhgthp vpsgkalvlq sqrtdfpyvs aampcfviii
301 ilcvpcckkk tsaaegp
```

SEQ. ID. NO. 11 MICB
```
  1 phslrynlmv lsqdgsvqsg flaeghldgq pflrydrqkr rakpqgqwae dvlgaetwdt
 61 etedltengq dlrrtlthik dqkgglhslq eirvceihed sstrgsrhfy yngelflsqn
121 letqestvpq ssraqtlamn vtnfwkedam ktkthyramq adclqklqry lksgvairrt
181 vppmvnvtcs evseqnitvt crassfyprn itltwrqdgv slshntqqwg dvlpdgngty
241 qtwvatrirq geeqkftcym ehsgnhgthp vpsgkalvlq sqrtdfpyvs aampcfviii
301 ilcvpcckkk tsaaegp
```

SEQ. ID. NO. 12 MICB
```
  1 phslrynlmv lsqdgsvqsg flaeghldgq pflrydrqkr rakpqgqwae dvlgaetwdt
 61 etedltengq dlrrtlthik dqkgglhslq eirvceihed sstrgsrhfy yngelflsqn
121 letqestvpq ssraqtlamn vtnfwkedam ktkthyramq adclqklqry lksgvairrt
181 vppmvnvtcs evseqnitvt crassfyprn itltwrqdgv slshntqqwg dvlpdgngty
241 qtwvatrirq geeqrftcym ehsgnhgthp vpsgkalvlq sqrtdfpyvs aampcfviii
301 ilcvpcckkk tsaaegp
```

FIGURE 6B

SEQ. ID. NO. 13 MICA
```
ephslrynlt vlswdgsvqs gfltevhldg qpflrcdrqk crakpqgqwa edvlgnktwd
retrdltgng kdlrmtlahi kdqkeglhsl qeirvceihe dnstrssqhf yydgelflsq
nletkewtmp qssraqtlam nvrnflkeda mktkthyham hadclqelrr ylksgvvlrr
tvppmvnvtr seasegnitv tcrasgfypw nitlswrqdg vslshdtqqw gdvlpdgngt
yqtwvatric qgeeqrftcy mehsgnhsth pvpsgk
```

SEQ. ID. NO. 14  DNA for SEQ. ID. NO. 13 MICA
```
gctagcgctg agagggtggc gacgtcgggg ccatgggct gggcccggtc ttcctgcttc
tggctggcat cttcccttt gcacctccgg gagctgctgc tgagccccac agtcttcgtt
ataacctcac ggtgctgtcc tgggatggat ctgtgcagtc agggtttctc actgaggtac
atctggatgg tcagcccttc ctgcgctgtg acaggcagaa atgcagggca aagccccagg
gacagtgggc agaagatgtc ctgggaaata agacatggga cagagagacc agGgacttga
cagggaacgg aaaggacctc aggatgaccc tggctcatat caaggaccag aaagaacgct
tgcattccct ccaggagatt agggtctgtg agatccatga agacaacagc accaggagct
cccagcattt ctactacgat ggggagctct tcctctccca aacctggaga ctaaggaatg
gacaatgccc cagtcctcca gagctcagac cttggccatg aacgtcagga atttcttgaa
ggaagatgcc atgaagacca agacacacta tcacgctatg catgcagact gcctgcagga
actacggcga tatctaaaat ccggcgtagt cctgaggaga acagtgcccc ccatggtgaa
tgtcacccgc agcgaggcct cagagggcaa cattaccgtg acatgcaggg cttctgcctt
ctatccctgg aatatcacac tgagctggcg tcaggatggg gtatctttga gccacgacac
ccagcagtgg gggatgtcc tgcctgatgg gaatggaacc taccagacct gggtggccac
caggatttgc caaggagagg agcagaggtt cacctgctac atggaacaca gcgggaatca
cagcactcac cctgtgccct ctgggaaaTA AAAGCTT
```

SEQ. ID. NO. 15    AV1401  5'-
    tatgaaatacctgctgccgaccgctgctgctggtctgctgctcctcgctgcccagcc-3'

SEQ. ID. NO. 16    AV1402  5'-
    catgggctgggcagcgaggagcagcagaccagcagcagcggtcggcagcaggtatttca-3'

SEQ. ID. NO. 17    AV1445  5'-
    catgcatcatcaccatcaccacctcgaggaattcaagcttggatccgc-3'

SEQ. ID. NO. 18    AV1446  5'-
    tcagcggatccaagcttgaattcctcgaggtggtgatggtgatgatg-3'

SEQ. ID. NO. 19    AV1466  5'-
    tttttgctagcgctgagagggtggcgacgtc-3'

SEQ. ID. NO. 20    AV1448  5'-
    ctttccaagcttttatttcccagagggcacagggtg-3'

SEQ. ID. NO. 21    AV1447  5'-
    tccctcctcgaggaaaacttgtactttcaaggcgagccccacagtcttcgttataacc-3'

FIGURE 6C

SEQ. ID. NO. 22    AV1408  5'-
    cccccggatccatgattactcatggttgttatacccg-3'

SEQ. ID. NO. 23    AV1409  5'-
    cccccaagcttattctacacaaaccgcatagac-3'

SEQ. ID. NO. 24    AV1602  5'-
    tttttctcgaggtggtgatggtgatgatgtcggccttcaataccgccgctggccttggtttgatc-3'

SEQ. ID. NO. 25    AV1603  5'-
    ccccccatatgattactcatggttgttatacccgg-3'

SEQ. ID. NO. 26    kk43  5'-
    aaaaaactcgaggaaaacttgtactttcaaggcacagtgccacccatggtgaatgtcacccgcag-3'

SEQ. ID. NO. 27    kk44  5'-
    atatataagcttttatttcccagagggcac-3'

SEQ. ID. NO. 28    kk52  5'-
    tttttcgtctctcatgattactcatggt-3'

SEQ. ID. NO. 29    kk45  5'-
    atatacatacagtcgaccaggttgggggcggtattgaaggccgacatc-3'

SEQ. ID. NO. 30    AV1466 5'-
    tttttgctagcgctgagagggtggcgacgtc-3'

SEQ. ID. NO. 31    AV1448 5'-
    ctttccaagcttttatttcccagagggcacagggtg-3'

SEQ. ID. NO. 32    AV1490 5'-
    aatcacagcactcaccctgtgccc-3'

SEQ. ID. NO. 33    AV1489 5'-
    tcccttcgtctctggtcggatacgctgtcgaacttttcgatc-3'

SEQ. ID. NO. 34    AV1493 5'-
    P-gaatcctggtggccacccaggtctgg-3'

SEQ. ID. NO. 35    AV1494 5'-
    P-gagacgacaaacgtctcttgctacatggaacacagcgggaatc-3'

FIGURE 6D

SEQ. ID. NO. 36   AV1826 5'-
gattagtggtggcagtggcggcggtagtcatcatcaccaccatcaccaccatcaccacagcggcggcagcggtggcggt-3'

SEQ. ID. NO. 37   AV1827 5'-
agcaaccgccaccgctgccgccgctgtggtgatggtggtgatggtggtgatgatgactaccgccgccactgccaccact-3'

SEQ. ID. NO. 38
SGGSGGGSHHHHHHHHHHSGGSGGG

FIGURE 6E

NON-NATURAL MIC PROTEINS

RELATED APPLICATIONS

This application claims priority from U.S. Provisional Application No. 61/291,749, filed Dec. 31, 2009, which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Mar. 23, 2011, is named CA2160.txt and is 41,414 bytes in size.

FIELD OF THE INVENTION

The instant invention relates generally to non-natural protein molecules that can recruit and activate NK cells, and more specifically to non-natural, monomeric, soluble, mammalian MHC class I chain-related (MIC) molecules modified within the α3 domain to contain a heterologous peptide that binds a target molecule on target cell.

BACKGROUND OF THE INVENTION

Natural killer (NK) cells and certain (CD8+ αβ and γδ) T-cells of the immunity system have important roles in humans and other mammals as first-line, innate defense against neoplastic and virus-infected cells (Cerwenka, A., and L. L. Lanier. 2001. NK cells, viruses and cancer. Nat. Rev. Immunol. 1:41-49). NK cells and certain T-cells exhibit on their surfaces NKG2D, a prominent, homodimeric, surface immunoreceptor responsible for recognizing a target cell and activating the innate defense against the pathologic cell (Lanier, L L, 1998. NK cell receptors. Ann. Rev. Immunol. 16: 359-393; Houchins J P et al. 1991. DNA sequence analysis of NKG2, a family of related cDNA clones encoding type II integral membrane proteins on human NK cells. J. Exp. Med. 173: 1017-1020; Bauer, S et al., 1999. Activation of NK cells and T cells by NKG2D, a receptor for stress-inducible MICA. Science 285: 727-730). The human NKG2D molecule possesses a C-type, lectin-like extracellular domain that binds to its cognate ligands, the 84% sequence identical or homologous, monomeric MICA [soluble form of MICA set forth in SEQ ID NOs: 1-6 and 13] and MICB [full protein of MICB set forth in SEQ ID NOs: 7-12], polymorphic analogs of the Major Histocompatibility Complex (MHC) Class I chain-related glycoproteins (MIC) (Weis et al. 1998. The C-type lectin superfamily of the immune system. Immunol. Rev. 163: 19-34; Bahram et al. 1994. A second lineage of mammalian MHC class I genes. PNAS 91:6259-6263; Bahram et al. 1996a. Nucleotide sequence of the human MHC class I MICA gene. Immunogentics 44: 80-81; Bahram and Spies T A. 1996. Nucleotide sequence of human MHC class I MICB cDNA. Immunogenetics 43: 230-233). Non-pathologic expression of MICA and MICB is restricted to intestinal epithelium, keratinocytes, endothelial cells and monocytes, but aberrant surface expression of these MIC proteins occurs in response to many types of cellular stress such as proliferation, oxidation and heat shock and marks the cell as pathologic (Groh et al. 1996. Cell stress-regulated human MHC class I gene expressed in GI epithelium. PNAS 93: 12445-12450; Groh et al. 1998. Recognition of stress-induced MHC molecules by intestinal γδT cells. Science 279: 1737-1740; Zwirner et al. 1999. Differential expression of MICA by endothelial cells, fibroblasts, keratinocytes and monocytes. Human Immunol. 60: 323-330). Pathologic expression of MIC proteins also seems involved in some autoimmune diseases (Ravetch, J V and Lanier L L. 2000. Immune Inhibitory Receptors. Science 290: 84-89; Burgess, S J. 2008. Immunol. Res. 40: 18-34). The differential regulation of NKG2D ligands, the polymorphic MICA (>50 alleles, see for examples SEQ. ID. NO. 1-6 and 13 of FIG. 6) and MICB (>13 alleles, see for examples SEQ. ID. NO. 7-12 of FIG. 6), is important to provide the immunity system with a means to identify and respond to a broad range of emergency cues while still protecting healthy cells from unwanted attack (Stephens H A, (2001) MICA and MICB genes: can the enigma of their polymorphism be resolved? Trends Immunol. 22: 378-85; Spies, T. 2008. Regulation of NKG2D ligands: a purposeful but delicate affair. Nature Immunol. 9: 1013-1015).

Viral infection is a common inducer of MIC protein expression and identifies the viral-infected cell for NK or T-cell attack (Groh et al. 1998; Groh et al. 2001. Co-stimulation of CD8+ αβT-cells by NKG2D via engagement by MIC induced on virus-infected cells. Nat. Immunol. 2: 255-260; Cerwenka, A., and L. L. Lanier. 2001). In fact, to avoid such an attack on its host cell, cytomegalovirus and other viruses have evolved mechanisms that prevent the expression of MIC proteins on the surface of the cell they infect in order to escape the wrath of the innate immunity system (Lodoen, M., K. Ogasawara, J. A. Hamerman, H. Arase, J. P. Houchins, E. S. Mocarski, and L. L. Lanier. 2003. NKG2D-mediated NK cell protection against cytomegalovirus is impaired by gp40 modulation of RAE-1 molecules. J. Exp. Med. 197:1245-1253; Stern-Ginossar et al., (2007) Host immune system gene targeting by viral miRNA. Science 317: 376-381; Stern-Ginossar et al., (2008) Human microRNAs regulate stress-induced immune responses mediated by the receptor NKG2D. Nature Immunology 9: 1065-73; Slavuljica, I A Busche, M Babic, M Mitrovic, I Gašparovic, Đ Cekinovic, E Markova Car, E P Pugel, A Cikovic, V J Lisnic, W J Britt, U Koszinowski, M Messerle, A Krmpotic and S Jonjic. 2010. Recombinant mouse cytomegalovirus expressing a ligand for the NKG2D receptor is attenuated and has improved vaccine properties. J. Clin. Invest. 120: 4532-4545).

In spite of their stress, many malignant cells, such as those of lung cancer and glioblastoma brain cancer, also avoid the expression of MIC proteins and as a result may be particularly aggressive as they too escape the innate immunity system (Busche, A et al. 2006, NK cell mediated rejection of experimental human lung cancer by genetic over expression of MHC class I chain-related gene A. Human Gene Therapy 17: 135-146; Doubrovina, E S, M M Doubrovin, E Vider, R B Sisson, R J O'Reilly, B Dupont, and Y M Vyas, 2003. Evasion from NK Cell Immunity by MHC Class I Chain-Related Molecules Expressing Colon Adenocarcinoma (2003) J. Immunology 6891-99; Friese, M. et al. 2003. MICA/NKG2D-mediated immunogene therapy of experimental gliomas. Cancer Research 63: 8996-9006; Fuertes, M B, M V Girart, L L Molinero, C I Domaica, L E Rossi, M M Barrio, J Mordoh, G A Rabinovich and N W Zwirner. (2008) Intracellular Retention of the NKG2D Ligand MHC Class I Chain-Related Gene A in Human Melanomas Confers Immune Privilege and Prevents NK Cell-Mediated Cytotoxicity. J. Immunology, 180: 4606-4614).

SUMMARY OF THE INVENTION

This invention describes soluble, monomeric, non-natural protein molecules that can recruit and activate NK cells and certain T-cells to attack specific cellular target cells by, after administration to a mammal, attaching the NKG2D-binding portions of MICA or MICB protein, i.e., their α1-α2 platform domain, specifically to the intended target molecule or molecules on the cellular target via a molecular targeting motif of the non-natural protein molecules of the invention. Accordingly, in one aspect of the invention there are provided non-natural, monomeric, soluble, mammalian MHC class I chain-related (MIC) molecules containing an α1-α2 platform domain attached to a targeting motif, wherein the targeting motif contains a MIC α3 domain and a heterologous peptide, wherein the heterologous peptide is inserted into the MIC α3 domain at a non-carboxy-terminal site, and wherein the heterologous peptide directs the binding of the targeting motif to a target molecule on a target cell, thereby delivering the attached α1-α2 platform domain to the target cell.

In some embodiments of the invention non-natural MIC proteins, the α1-α2 platform domain and the α3 domain are from a human MIC protein. In particular embodiments, the α1-α2 platform domain and the α3 domain are from a human MICA protein selected from the group consisting of SEQ ID NOs:1-6, and 13. In other embodiments, the α1-α2 platform domain and the α3 domain are from a human MICB protein selected from the group consisting of SEQ ID NOs:7-12.

In certain embodiments, the α3 domain of the non-natural MIC molecule is a complete native α3 domain without a deletion. In other embodiments α3 domain is a complete native α3 domain, wherein a portion of the domain has been deleted. In some embodiments, the portion deleted from the α3 domain is adjacent to the insertion site of the heterologous peptide. In other embodiments, the α3 domain comprises a deletion, insertion, amino acid substitution, mutation, or combination thereof at site different from the insertion site.

In particular embodiments of the non-natural MIC molecules, the insertion of the heterologous peptide is within or adjacent to a solvent-exposed loop of the α3 domain. In certain embodiments, the solvent-exposed loop corresponds to amino acids numbers 191-196, 208-211, 221-228, 231-240, 249-254, or 264-266 of the α3 domain within a MIC protein selected from the group consisting of SEQ ID NOs: 1-13. In preferred embodiments, the insertion is in a solvent-exposed loop corresponding to amino acids numbers 191-196, 221-228, or 249-254 of the α3 domain within a MIC protein selected from the group consisting of SEQ ID NOs: 1-13.

In some embodiments of the invention, the target molecule is a cell-surface molecule. In particular embodiments, the cell-surface molecule is on the surface of a malignant cell or a virus infected cell.

In particular embodiments in which the target cell is malignant, the target molecule is a human epidermal growth factor receptor 2 (HER2), NK-1R, epidermal growth factor receptor (EGFR), Erb2 or melanoma antigen; a growth factor receptor, an angiogenic factor receptor, an integrin, or an oncogene-encoded protein product, or a fragment thereof.

In embodiments in which the target cell is infected by a virus, the target molecule on the target cell is a phosphotidylserine, or a phosphotidylserine with an accessory protein; or a surface glycoprotein encoded by a virus, an adenovirus, a human immunodeficiency virus, a herpetic virus, a pox virus, a flavivirus, a filovirus, a hepatitis virus or a papilloma virus.

In another aspect of the invention, there are provided compositions containing the non-natural MIC molecules of the invention and a carrier or excipient.

In a further aspect of the invention, there are provided nucleic acid molecules encoding the non-natural MIC molecules of the invention. In particular embodiments, there are provided nucleic acid molecules encoding non-natural, monomeric, soluble, mammalian MHC class I chain-related (MIC) molecules containing an α1-α2 platform domain attached to a targeting motif, wherein the targeting motif contains a MIC α3 domain and a heterologous peptide, wherein the heterologous peptide is inserted into the MIC α3 domain at a non-carboxy-terminal site, and wherein the heterologous peptide directs the binding of the targeting motif to a target molecule on a target cell, thereby delivering the attached α1-α2 platform domain to the target cell. In some embodiments of the invention, the nucleic acid molecules encode non-natural MIC proteins, having α1-α2 platform domain and the α3 domain are from a human MICA protein selected from the group consisting of SEQ ID NOs:1-6, and 13 or a human MICB protein selected from the group consisting of SEQ ID NOs:7-12. In particular embodiments of the nucleic acid molecules encoding non-natural MIC molecules, a polynucleotide encoding a heterologous peptide is inserted within or adjacent to the nucleic acid sequence encoding a solvent-exposed loop of the α3 domain corresponding to amino acids numbers 191-196, 208-211, 221-228, 231-240, 249-254, or 264-266 of the α3 domain within a MIC protein selected from the group consisting of SEQ ID NOs:1-13. In preferred embodiments, the insertion is in the nucleic acid sequence encoding a solvent-exposed loop corresponding to amino acids numbers 191-196, 221-228, or 249-254 of the α3 domain within a MIC protein selected from the group consisting of SEQ ID NOs:1-13.

In another aspect of the invention, there are provided libraries containing non-natural MIC molecules of the invention, in which the members of a library have diverse individual target binding properties.

In still another aspect of the invention, there are provided libraries containing genes encoding the non-natural MIC molecules of the invention, in which the members of a library have diverse individual target binding properties.

In still another aspect of the invention, there are provided methods of treating a mammal suspected of having a malignancy or viral infection by administering an effective amount of the a non-natural MIC molecule of the invention to the mammal, wherein the heterologous peptide directs binding of the targeting motif to the target molecule on a malignant cell or a virus-infected cell. In certain embodiments, the non-natural MIC molecule binds a NKG2D-bearing cell and a malignant cell or a virus-infected cell, resulting in the adhesion of the NKG2D-bearing cell to the malignant cell or the virus-infected cell. In particular embodiments, the adhering NKG2D-bearing cell destroys the malignant cell or the virus-infected cell.

BRIEF DESCRIPTION OF THE DRAWINGS

FIG. 1 shows the structure of the soluble form of human MICA. The human MICA structure is represented as ribbons (Li et al., Nature Immunology 2:443-451, 2001). The α1 and α2 domains provide the binding sites for the NKG2D homodimer. The α3 domain is a member of the Ig superfamily and is in this soluble form expressed in *E. coli* contains the C-terminus.

FIG. 2 shows a schematic of a DGR-based approach for diversifying the α3 domain of human MICA.

FIG. 3 shows a schematic of EaeA and the EaeA-α3 fusion protein displayed on the surface of *E. coli*.

FIG. 4 shows a photograph of the SDS-PAGE analysis of the cytosolic ("cytosol"), cytoplasmic membrane ("Cytopl memb"), and outer membrane ("Outer memb") proteins from induced (lanes labeled "B") or un-induced (lanes labeled "A") cultures of *E. coli* harboring pKK29 detected by Coomassie blue staining or Western blotting with an antibody against human MICA. The molecular weights are indicated. The fusion of MICA α3 domain to intimin (EaeA) is expressed on the outer membrane of the *E. coli* cells induced with arabinose.

FIGS. 6A-6E provide the amino acid or nucleic acid sequences for SEQ ID NOs: 1-38.

DETAILED DESCRIPTION OF THE INVENTION

Figure 5:
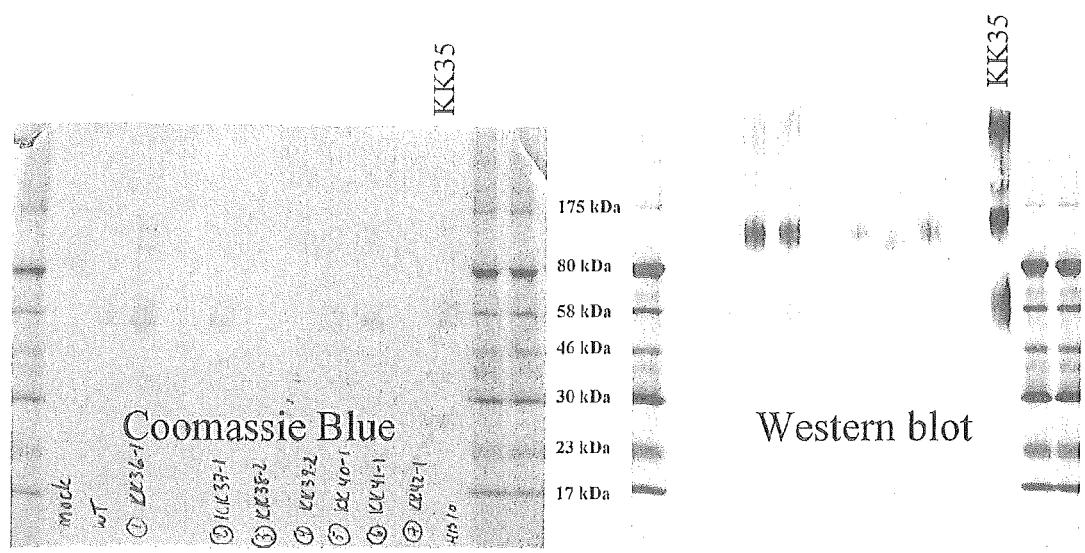
FIG. 5 shows a photograph of the SDS-PAGE analysis of proteins secreted by 293T cells transiently transfected with plasmids pKK35 through pKK42 as detected by Coomassie blue staining or Western blotting with an antibody against human MICA. Samples applied were concentrated from the supernatants of 293T cells transiently transfected with the indicated plasmids. The lanes marked KK35 were loaded with protein that bound to the target Ni-NTA after being secreted by 293T cells transfected with pKK35. The molecular weights of the marker proteins are indicated.

This invention describes soluble, monomeric, non-natural protein molecules that can recruit and activate NK cells and certain T-cells to attack specific cellular target cells by, after administration to a mammal, binding of the NKG2D-binding portions of MICA or MICB protein, i.e. their α1-α2 platform domain (amino acids 1-85 and 86-178, for the α1 domain and the α2 domain, respectively), to the intended target molecule or molecules specifically via a targeting motif attached to α1-α2 platform domain. The targeting motif includes an α3 domain of a MICA or MICB protein and a heterologous peptide that binds the target molecule. A "heterologous peptide" is a peptide that is not naturally or normally within the α3 domain. In some embodiments, the heterologous peptide is integral to one of the solvent-exposed loops of the soluble MICA or MICB α3 domain. An integral heterologous peptide can be a non-terminal component of the MICα3 domain and direct the binding of the MICα3 domain to a target molecule. In particular embodiments, the heterologous peptide can include a portion of a complement-determining region of a natural or recombinant antibody, another protein or peptide molecule or binding motif, a polysaccharide or other carbohydrate, a nucleic acid or synthetic analog of a nucleic acid. In certain embodiments, the heterologous peptide is a complement-determining region of an antibody. The incorporation of a heterologous peptide results in an unnatural, modified or converted α3 domain of a MICA or MICB protein, which acquires the useful function of directing the targeting the α1-α2 platform based on the binding properties (e.g., cognate binding partner) of the heterologous peptide. The non-natural, monovalent molecules of the invention have the distinct advantage of not being linked or restricted to a common presenting surface and thereby can be modified, formulated and administered to a mammal as traditional biopharmaceuticals.

The modifications to the α3 domain desired include those that add or increase the specificity or sensitivity of the binding of the α3 domain to a target molecule, such as a molecule on the surface of a target cell, for example, a malignant cell or virus-infected cell. The α1-α2 platform domain is tethered to the modified targeting α3 domain and is diffusible in the intercellular or intravascular space of the mammal. Preferably the α1-α2 platform domains of the non-natural MIC proteins of the invention are at least 80% identical or homologous to a native or natural α1-α2 domain of a human MICA or MICB protein and binds an NKG2D receptor. In some embodiments, the α1-α2 platform domain is 85% identical to a native or natural α1-α2 platform domain of a human MICA or MICB protein and binds an NKG2D receptor. In other embodiments, the α1-α2 platform domain is 90%, 95%, 96%, 97%, 98%, or 99% identical to a native or natural α1-α2 platform domain of a human MICA or MICB protein and binds an NKG2D receptor. Exemplary human MICA proteins (soluble form) include SEQ ID NOs: 1-6 and 13. Exemplary human MICB proteins (full protein) include SEQ ID NOs: 7-12.

As used herein, the "soluble form of a MIC protein" refers to a MIC protein containing the α1, α2, and α3 domains of the full MIC protein. Exemplary soluble forms of the MIC proteins include amino acid residues 1-274 or 1-276 of SEQ ID NOs:1-13.

As used herein, the "full MIC protein" refers to a MIC protein containing the α1, α2, and α3 domains, the transmembrane domain, and the intracellular domain. Exemplary full MICB proteins are set forth in SEQ ID NOs:7-12.

The invention further provides a library of MIC genes or resulting soluble MIC proteins, wherein each member of the library has or exhibits a different property, such as its binding property for the target cell, resulting in a library of diverse molecules. For example, the library can contain diverse individual target binding properties representing 10 or more different binding specificities. As used herein, "diverse individual target binding properties" refers to a library of MIC proteins, in which the individual members of the library bind to a different target molecule or have different affinities for the same target molecule. In some libraries of MIC proteins, two or more members may bind the same target but may have different binding affinities.

In a further embodiment of the invention, a mammal having a malignancy or a viral infection can be treated by administering an effective amount of the soluble MIC protein to affect the malignant or viral condition. The administration of the molecule to the mammal may result in the adhesion of NKG2D-bearing NK cells or T-cells to the target malignant or virus-infected cell, wherein the NK cell or T-cell destructively attacks or destroys the target malignant or virus-infected cell.

The invention also includes the means of converting the α3 domain (for example amino acids 182-274, in SEQ ID NO. 1-13) of a MIC protein into a specific targeting domain that can directly deliver from the intercellular space its tethered α1-α2 domain to the target cell surface in order to attract or bind the NKG2D-bearing NK cell or T-cell.

Applications of these "passive vaccines" are to destroy pathologic cells that, in spite of being pathologic, do not express the appropriate level of ligands, such as MICA or MICB, that are necessary to attract NK cells or certain T-cells. For example, only 30% of human lung cancers express MICA (Busche, A et al. 2006). Glioblastoma cells over express an NK cell inhibitory signal that prevents innate immunity attack; however, over expressing the natural MICA gene product in lung cancer or glioblastoma cells in experimental animals, restores effective NK cell attack on the cancer (Friese, M. et al. 2003).

The high resolution structure of human MICA bound to the NKG2D receptor has been solved and demonstrates that the α3 domain of MICA has no direct interaction with the NKG2D receptor (Li et al. 2001. Complex structure of the activating immunoreceptor NKG2D and its MHC class I-like ligand MICA. Nature Immunol. 2: 443-451; Protein Data Bank accession code 1HYR). The α3 domain of MICA, like that of MICB, is connected to the α1-α2 platform domain by a short, flexible linker peptide, amino acids 175-182 [SEQ ID 1-13], and itself is positioned naturally as "spacer" between the platform and the surface of the MIC expressing cell. The 3-dimensional structures of the human MICA and MICB α3 domains are nearly identical (root-mean square distance<1 Å on 94 C-α's) and functionally interchangeable (Holmes et al. 2001. Structural Studies of Allelic Diversity of the MHC Class I Homolog MICB, a Stress-Inducible Ligand for the Activating Immunoreceptor NKG2D. J Immunol. 169: 1395-1400).

Furthermore, the 3-dimensional structures of the MIC protein's Ig-like α3 domains resemble that of Tendamistat, and in a sequence inverted form, that of the human tenth fibronectin domain III; both structures have served as scaffolds for engineering protein binding motifs (Pflugrath, J W, G Wiegand, R Huber, L Vértesy (1986) Crystal structure determination, refinement and the molecular model of the α-amylase inhibitor Hoe-467A. J. Molec. Biol. 189: 383-386; Koide A, Bailey C W, Huang X, Koide S. 1998. The fibronectin type III domain as a scaffold for novel binding proteins. J. Mol. Biol. 284: 1141-1151; Li, R, R H Hoess, J S Bennett and W F DeGrado (2003) Use of phage display to probe the evolution of binding specificity and affinity in integrins. Protein Engineering 16: 65-72; Lipovsek, D. et al. (2007) Evolution of an interloop disulfide bond in high-affinity antibody mimics based on fibronectin type III domain and selected by yeast surface display: molecular convergence with single-domain camelid and shark antibodies. J. Mol Biol 368: 1024-1041; U.S. Pat. No. 7,153,661; Protein Data Bank accession code 1TTG).

One aspect of the invention contemplates engineering specific binding properties into 1 or more of the 6 solvent-exposed loops of the α3 domain of MICA or MICB, a soluble, non-natural MIC molecule is created that after administration to a mammal can diffuse in the intravascular or intercellular space and subsequently attach with high sensitivity and specificity to a target molecule on an intended target cell and, thereby promote binding and subsequent destructive attack of the particular target cell by NKG2D-bearing NK and/or T-cells. Examples of surface accessible molecules on target malignant cells include integrins, oncogene products or fragments thereof, such as NK-1R, human epidermal growth factor 2 (Her2 or ErbB2), growth factor receptors such as Epidermal Growth Factor Receptor (EGFR), angiogenic factor receptors such as those for vascular endothelial growth factor (VEGF) receptor and VEGF-related molecules, melanoma antigens, and antigens of LNcaP and PC-3 prostate cancer cells. The surface accessible molecules on target virus-infected cells include "inside-out" phosphotidylserine with or without accessory proteins such as apolipoprotein H, Gas6, MFG-E8; virus-encoded antigens, virus-encoded antigens of hepatitis viruses; adenoviruses; cytomegalovirus; other herpetic viruses; HIV especially p17; vaccinia; pox viruses; rotavirus; influenza; parvo viruses; West Nile virus; rabies; polyoma; papilloma viruses; rubella; distemper virus; and Japanese encephalitis virus (Balasubramanian, K and Schroit, A J. 2003. Ann. Rev. Physiol. 65: 701-734; Soares, M M, S W King & P E Thorpe. (2008) Targeting inside-out phosphatidylserine as a therapeutic strategy for viral diseases. Nature Medicine 14: 1358-62; Slavuljica et al., 2010). The present compositions can be produced by introducing specific binding motifs into the α3 domain of MICA or MICB deploying synthetic DNA, bacteriophage display or yeast or bacterial surface display technology, several of which have been deployed to create specific binding properties in Tendamistat and the human tenth fibronectin domain III (McConnell, S J and R H Hoess, (1995) Tendamistat as a Scaffold for Conformationally Constrained Phage Peptide Libraries. J. Molec. Biol 250: 460-470; Li et al. (2003); Sidhu, S. S. & S. Koide (2007) Phage display for engineering and analyzing protein interaction interfaces. *Current Opinion in Struct. Biol.* 17: 481-487; Lipovsek, D. et al. 2007). These methods involve making a library of α3 domain structures that are highly diversified within their solvent-exposed loops and from which to isolate those that exhibit the desired binding properties by selection, screening or panning, all well known to those ordinarily skilled in the art.

The diversity generating retroelements (DGR) of Miller et al. is an example of a method of generating diversity at desired amino acid positions within the loops (Medhekar, B. & J. F. Miller. 2007. Diversity-Generating Retroelements. Current Opinion in Microbiol. 10: 388-395 and U.S. Pat. No. 7,585,957, which is incorporated herein by reference). Because the α3 domains of human MICA and MICB are comprised of about 95 amino acids (182-276) of the 276 amino acid water-soluble form, all solvent-exposed loops, for example amino acids 191-196, 208-211, 221-228, 231-240, 249-254, or 264-266 of SEQ. ID. NO. 1-13, can be diversified and even expanded with inserted amino acids by homing mutagenesis deploying a synthetic Template Repeat (TR) of a length not exceeding 200 nucleotides, a length known to be operable (Guo, H et al. 2008. Diversity-Generating Retroelement Homing Regenerates Target Sequences for Repeated Rounds of Codon Rewriting and Protein Diversification. Molecular Cell 31, 813-823).

Several factors guide the creation of the DGR-based library of diversified, solvent-exposed loops of the α3 domain.

DGRs generate diversity in defined segments of protein-encoding DNA sequences, designated as variable repeats (VRs). For some heterologous sequences to function as VRs, they are flanked at their ends by initiation of mutagenic homing (IMH) sequences. The IMH sequences serve as cis-acting sites that direct mutagenic homing and determine the 3' boundary of sequence diversification.

The 5' boundary of VR diversification may be determined by the extent of homology between VR and its cognate TR. Only partial homology is required and mismatches are tolerated.

Specific sites in VR which are subject to diversification may be determined by the location of adenine residues in TR. By inserting adenine residues at appropriate locations within "synthetic" TRs, specific VR-encoded amino acid residues can be diversified.

The atd protein, the TR-encoded RNA intermediate, and the RT reverse transcriptase efficiently function in trans when expressed on a plasmid vector, pDGR, under the control of a heterologous promoter, for example, $P_{tetA}$ or $P_{bad}$. This provides a convenient means for turning on and off diversification within a bacterial cell and convenient access to the synthetic TR sequences to program the precise sites to be diversified. Furthermore, high level expression of trans-acting components results in highly efficient diversification.

A general outline of the DGR-based approach for diversifying the α3 domain is shown in FIG. 2. The sequences to be diversified correspond to the loops of α3 domain. An IMH sequence is positioned immediately downstream from the stop codon (about AV277) of the gene encoding α3 domain, creating a "synthetic VR" which will be subject to diversification.

The synthetic VR encoding the α3 domain will be diversified by the synthetic TR on plasmid pDGR (FIG. 2). This TR element includes an IMH* and upstream sequences that are homologous to VR. The specific VR residues that will be subject to mutagenesis are precisely programmed by the placement of adenines in TR, and high densities of adenine residues can be tolerated by the system. The pDGR also includes loci which encode Atd and the RT reverse transcriptase. Atd, TR and rt are expressed from the tightly regulated tetA promoter/operator ($P_{tetA}$), which allows precise control over the diversification process by the addition or removal of anhydotetracycline.

It is instructive to consider diversifying the α3 domain via the DGR mechanism in a standard phage display format. In this case, the α3 domain is fused to a filamentous phage coat protein encoded on a phagemid vector in *E. coli*. VR would include solvent-exposed loops of the α3 domain, and pDGR would be designed to efficiently diversify VR at specified locations within those loops (Guo et al. 2008). Activating atd, TR, and rt expression would mutagenize VR sequences present on phagemid genomes. This would result in the creation of a library of phage, each of which presents a diversified binding protein on its surface and packages the encoding DNA. Desired specificities would be selected by binding phage to the immobilized target molecule, for example the surface exposed protein product of oncogene Her2, washing to remove nonbinding phage, and reamplification and enrichment. Further rounds of optimization of the selected phenotype could be efficiently accomplished by simply infecting *E. coli* containing pDGR with the selected or panned phage and repeating the steps described above. This system is capable of generating library sizes that are several orders of magnitude greater than those achieved by conventional approaches. Of equal advantage is the extraordinary ease with which successive rounds of optimization may be achieved with cumulative improvements, but without compromise of the integrity of the α3 domain scaffold.

Displaying diversified proteins on the surface of bacteria, such as *Escherichia coli*, is an alternative approach that offers potential advantages over phage display. For example, successive rounds of optimization can be achieved without the need to make any phage or to cycle selected phage through multiple rounds of infection. And the α3 domain can be designed to be cleaved from the bacterial surface for direct biochemical or physical analyses. Although DGRs are found naturally in the genomes of over 40 bacterial species, none has been identified in *E. coli*. However, recently the cis and trans-acting components of a DGR from *Legionella pneumophila* have been shown by Miller et al to efficiently function in *E. coli*. Diversified α3 domains of MICA or MICB will be expressed on the surface of *E. coli* as fusion proteins consisting of, as a non-limiting example, the outer membrane localization and anchor domains of the EaeA intimin protein encoded by enteropathogenic *E. coli* (Luo Y, Frey E A, Pfuetzner R A, Creagh A L, Knoechel D G, Haynes C A, Finlay B B, Strynadka N C. (2000) Crystal structure of enteropathogenic *Escherichia coli* intimin-receptor complex. *Nature.* 405:1073-7). EaeA consists of an N-terminal segment of approximately 500 amino acids that anchors the protein to the outer membrane and is believed to form an anti-parallel β-barrel with a porin-like structure that facilitates translocation (Touze T, Hayward R D, Eswaran J, Leong J M, Koronakis V. (2004) Self-association of EPEC intimin mediated by the beta-barrel-containing anchor domain: a role in clustering of the Tir receptor. *Mol Microbiol.* 51:73-87). This translocation domain is followed by a series of Ig-like motifs and a C-terminal C-type lectin domain responsible for binding to the intestinal epithelial surface (FIG. 3). The elongated structure of intimin and its ability to export and anchor a heterologous protein domain to the external face of the *E. coli* outer membrane suggest that it is an ideal and versatile fusion partner for surface display of diversified α3 proteins (Wentzel A, Christmann A, Adams T, Kolmar H. (2001). Display of passenger proteins on the surface of *Escherichia coli* K-12 by the enterohemorrhagic *E. coli* intimin EaeA. J Bacteriol. 183: 7273-84; Adams, T M, A Wentzel, and H Kolmar (2005) Intimin-Mediated Export of Passenger Proteins Requires Maintenance of a Translocation-Competent Conformation. J. of Bacteriology, 187: 522-533).

The natural orientation of MICA and MICB is such that the C-terminus is anchored to the cell membrane (type I membrane protein). The α3 domain resides between the N-terminal α1-α2 platform and the cell membrane. However, to diversify those α3 domain loops that project away from the α1-α2 platform, the opposite orientation (e.g. type II membrane protein) is desired, that is, to attach the N-terminus the linker portion of the α3 domain in FIG. 1 to EaeA so that those loops such as those located at amino acid positions 191-196, 221-228, 253-256 [SEQ. ID. NO. 1-13] are readily available for binding target molecules. Such a type II membrane protein orientation is precisely that of EaeA, FIG. 3. Furthermore, the α3 domain, like EaeA, has an Ig-like motif, so that EaeA will translocate α3 domains to the *E. coli* surface (Li et al. 1999. Crystal structure of the MHC class I homolog MICA, a γδT cell ligand. Immunity 10: 577-584). Indeed, the ability of EaeA to translocate heterologous passenger polypeptides has been documented in the literature (Wentzel et al. 2001; Adams et al., 2005).

The EaeA-α3 fusion protein will be expressed from the araBAD promoter ($P_{bad}$), which responds, in a dose-dependent manner, to the concentration of arabinose added to the growth media. This will allow precise control over the density of α3 domains on the surface of bacterial cells. A diversification system, e.g. the *L. pneumophila* atd TR rt sequences (pDGR, FIG. 2), can be placed under control of the tightly regulated tetA promoter/operator on a multicopy plasmid. The expression of the atd TR rt sequences is induced by addition of anhydrotetracycline to the growth medium and will result in high frequency diversification of α3 VR sequences. Once diversification has been achieved, removal of inducer from the growth media will "lock" the system (α3-VR) into a stable state.

Diversification is first achieved by growing the surface display *E. coli* in the presence of arabinose to induce expression of the EaeA-α3 fusion protein, and anhydrotetracycline to induce diversification of α3-VR. Bacterial cells that display binding characteristics of interest can be enriched using standard methods such as Fluorescent Activated Cell Sorting (FACS) or magnetic bead separation techniques. Selected bacterial cells are amplified by growth in the presence of arabinose and the absence of anhydrotetracycline. Further enrichment steps can be included and additional rounds of optimization can be achieved by simply repeating the protocol. Importantly, α3 domains that bind to targets that are undesirable for NK or T-cell attack can be depleted from the diversified library by palming against, for example, normal tissues prior to selection for the desired binding properties. The selected α3 proteins can be cleaved from the bacterial cell surface by the addition of Factor Xa protease and then purified by affinity purification of the 6×His-tagged (SEQ ID NO: 39) C-terminal domain for further characterization and use. This permits convenient biochemical and physical analyses of structure and function of the selected α3 domain. By fusing the isolated DNA encoding the desired, non-natural α3 domain to the portion of the MIC gene encoding an α1-α2 platform domain, the desired, non-natural α3 domain can then in each case be reintroduced into the rest of the soluble MIC protein via its linker or tether (amino acids 177-182) to create the desired passive NK cell vaccine with the specificity and sensitivity of the isolated α3 domain.

The isolated, non-natural or unnatural, soluble MIC protein can be produced in bacteria, yeasts or mammalian cells, purified to the required degree, formulated by available methods to stabilize it in vitro and in vivo, and administered parenterally or by other routes to humans or other mammals where it can diffuse to treat malignancies or viral diseases by promoting the targeted attack by the cellular components of the innate immunity system.

In some embodiments, a non-natural MIC molecule is formulated with a "pharmaceutically acceptable" excipient or carrier. Such a component is one that is suitable for use with humans or animals without undue adverse side effects. Non-limiting examples of adverse side effects include toxicity, irritation, and/or allergic response. The excipient or carrier is typically one that is commensurate with a reasonable benefit/risk ratio. In many embodiments, the carrier or excipient is suitable for topical or systemic administration. Non-limiting pharmaceutically carriers include sterile aqueous or non-aqueous solutions, suspensions, and emulsions. Examples include, but are not limited to, standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyloleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Optionally, a composition comprising a non-natural MIC molecule of the disclosure may also be lyophilized using means well known in the art. Subsequent reconstitution and use may be practiced as known in the field.

Also provided are formulations comprising microencapsulated non-natural MIC molecules. In some embodiments, these may provide sustained release kinetics or allow oral ingestion to pass through the stomach and into the small or large intestine. In general, the pharmaceutical compositions can be prepared in various forms, such as granules, tablets, pills, suppositories, capsules (e.g. adapted for oral delivery), microbeads, microspheres, liposomes, suspensions, salves, pastes, lotions, and the like. Pharmaceutical grade organic or inorganic carriers and/or diluents suitable for oral and topical use can be used to make up compositions comprising the therapeutically-active compounds. Stabilizing agents, wetting and emulsifying agents, salts for varying the osmotic pressure, or buffers for securing an adequate pH value may be included.

A non-natural MIC molecule is typically used in an amount or concentration that is "safe and effective", which refers to a quantity that is sufficient to produce a desired therapeutic response without undue adverse side effects like those described above. A non-natural MIC molecule may also be used in an amount or concentration that is "therapeutically effective", which refers to an amount effective to yield a desired therapeutic response, such as, but not limited to, an amount effective to bind target cells in order to recruit sufficient NK cells to kill the target cells. The safe and effective amount or therapeutically effective amount will vary with various factors but may be readily determined by the skilled practitioner without undue experimentation. Non-limiting examples of factors include the particular condition being treated, the physical condition of the subject, the type of subject being treated, the duration of the treatment, the nature of concurrent therapy (if any), and the specific formulations employed.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

All references cited herein are hereby incorporated by reference in their entireties, whether previously specifically incorporated or not. As used herein, the terms "a", "an", and "any" are each intended to include both the singular and plural forms.

Having now fully described the invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and may be applied to the essential features hereinbefore set forth.

EXAMPLES

1. Display of MIC-α3 Domain Protein on the Surface of *E. coli*

Oligonucleotides AV1401 (SEQ. ID. NO. 15) and AV1402 (SEQ. ID. NO. 16) were kinased, annealed, and ligated into an aliquot of plasmid pET30a (Novagen) which had been digested with NdeI and NcoI to create pSW249, containing a pelB secretion signal sequence.

Plasmid pSW249 was digested with NcoI and BlpI and ligated together with kinased and annealed oligonucleotides AV1445 (SEQ. ID. NO. 17) and AV1446 (SEQ. ID. NO. 18) to create pSW263. This construct contained sequence encoding six histidine residues (SEQ ID NO: 39) following the pelB sequence.

A human MICA cDNA comprising a portion of 5' untranslated sequence, signal sequence, and codons 1-276 of the mature coding sequence, followed by a stop codon, was amplified by PCR from human spleen first strand cDNA (acquired from Invitrogen) using primers AV1466 (SEQ. ID. NO. 19) and AV1448 (SEQ. ID. NO. 20).

The PCR fragment was digested with NheI and HindIII and ligated together with pCDNA5-FRT (Invitrogen) which had also been digested with NheI and HindIII to create pSW265. Three mutations the MICA coding region were corrected, G14W, A24T and E125K, by directed mutagenesis to create pSW271.

A portion of pSW271 was PCR amplified with primers AV1447 (SEQ. ID. NO. 21) and AV1448 (SEQ. ID. NO. 20). The PCR fragment consisted of a tev protease cleavage site, ENLYFQG (SEQ ID NO: 40), followed by codons 1-276 of human MICA. This PCR fragment was digested with XhoI and HindIII and ligated together with an aliquot of plasmid pSW263 which had also been digested with XhoI and HindIII to create plasmid pSW286.

The eaeA gene was amplified from EDL933 genomic DNA using AV1408 (SEQ. ID. NO. 22) and AV1409 (SEQ. ID. NO. 23) primers.

This PCR product was digested with BamHI and HindIII and ligated together with Bluescript-SK+ DNA (Stratagene) which had also been digested with BamHI and HindIII to create pSW284.

A portion of plasmid pSW284 was PCR amplified using primers AV1602 (SEQ. ID. NO. 24) and AV1603 (SEQ. ID. NO. 25). The PCR fragment was digested with NdeI and XhoI and ligated together with an aliquot of pSW286 which had also been digested with NdeI and XhoI to create pSW289.

A portion of pSW289 was PCR amplified with primers kk43 (SEQ. ID. NO. 26) and kk44 (SEQ. ID. NO. 27). The resulting PCR fragment containing a tev protease cleavage site, ENLYFQG (SEQ ID NO: 40), followed by sequence encoding residues 181 through 276 of MICA (note: the codon for P183 WAS changed from CCC to CCA to break up a run of 6 C's) was digested with XhoI and HindIII and ligated together with a ~7185 bp fragment which had been purified on an agarose gel from a digest of a separate aliquot of pSW289 digested with XhoI and HindIII to create pKK5. The 7185 bp fragment encoded EaeA 1-659 followed by GG then a factor Xa cleavage site, IEGR (SEQ ID NO: 41), then six His residues (SEQ ID NO: 39), then an XhoI site encoding LE of no function except to provide the XhoI site.

pKK5 was PCR amplified with primers kk52 (SEQ. ID. NO. 28) and kk45 (SEQ. ID. NO. 29). The PCR fragment was digested with NcoI and HindIII and ligated together with an aliquot of pBAD24 (from ATCC) which had been digested with NcoI and HindIII to create pKK29. The plasmid pKK29 was transformed according to the manufacturer's recommendations into the cloning strain, E. coli "NEB 10-beta" (catalog AV C3019H from New England BioLabs) and selected for resistance to 100 µg/ml carbenicillin.

Cytosolic proteins, inner membrane proteins, and outer membrane proteins of arabinose-induced and non-induced pKK29-transformed E. coli cells were each isolated and analyzed by SDS-PAGE. The SDS-PAGE gels were stained with Coomassie blue or western-blotted with antibody to human MICA protein.

Cells were grown in LB/Carb100 until $OD_{600}$=0.915. Aliquots of 10 mls of cells were added to each of two 50 ml conical tubes. One tube was induced with 0.002% arabinose; the other was left un-induced. Samples were incubated with shaking @37° C. for 1 hr.

Cells were then centrifuged for 10 min at 4000 rpm in an Eppendorf 5810R tabletop centrifuge. Supernatants were discarded and the cell pellets were gently resuspended in 6 ml FP buffer (0.1 M sodium phosphate buffer pH 7.0, 0.1 M KCl, 5 mM EDTA, 1 mM dithiothreitol, 1 mM phenylmethylsulfonyl fluoride) and transferred to 15 ml conical tubes. Cells were sonicated for 6×15 sec bursts using a Biologics Inc model 300 V/T ultrasonic homogenizer. Samples were incubated on ice between bursts. After sonication the tubes were centrifuged in the Eppendorf 5810R tabletop centrifuge at 4000 rpm for 5 minutes to remove any unbroken cells.

Supernatants were transferred to Beckman polycarbonate centrifuge tubes (catAV355631) and spun at 100,000×g for 1 hr at 4° C. in a Beckman L8-80M floor ultracentrifuge using a Type 60Ti rotor. The supernatants containing the cytosolic proteins were removed to new tubes and stored at 4° C.

The pellets of the cell membranes were resuspended in 2 mls of ME buffer (10 mM Tris-HCl pH 8.0, 35 mM MgCl2, 1% Triton X-100). Samples shook gently for 2 hrs at 25° C. and then were re-centrifuged in the Beckman L8-80M floor ultracentrifuge using a Type 60Ti rotor at 100,000×g for 30 min at 4° C. Supernatants containing the cytoplasmic membrane Triton-soluble proteins were removed to new tubes and stored at 4° C. The final pellets containing the outer membrane proteins (Schnaitman, C A. 1971. Solubilization of the Cytoplasmic Membrane of *Escherichia coli* by Triton X-100. J. Bacteriology 108: 545-552) were resuspended in 0.1 ml of water and also stored at 4° C. before being subjected to analyses by SDS-PAGE and stained by Coomassie Blue or western blotted using a goat polyclonal antibody against human MICA, FIG. 4.

Samples were mixed with equal volumes of Novex Tris-Glycine SDS 2× sample buffer (Invitrogen AVLC2676) and electrophoresed on 4-20% Tris-Glycine Gradient Gel (Invitrogen AVEC60285BOX). For western blotting the electrophoresed sample lanes in the slab gel were transferred to a nitrocellulose membrane (Invitrogen Nitrocellulose Membrane Filter Paper Sandwich AVLC2001) using an Invitrogen XCell II Blot Module (AVEI9051). The membrane filter was blocked overnight at 4° C. in 5% milk-Phosphate Buffered Saline, Tween-20 (PBST). Primary antibody (anti-human MICA antibody—R&D Systems AVAF1300) was used at 1:500 dilution in 5% milk-PBST. The resulting filter "blot" was incubated 2 hrs at 25° C. with gentle rocking The filter "blot" was subsequently washed for 20 min at 25° C. with PBST after which the secondary antibody (anti-goat IgG-HRP antibody—R&D Systems AVHAF017) was added at a dilution of 1:1000 in 5% milk-PBST. The filter "blot" was rocked for 2 hrs at 25° C. and then again was washed 20 min in PBST. The filter "blot" was developed with Novex HRP Chromogenic Substrate—TMB (Invitrogen AVWP20004).

2. Generation of Soluble, Non-Natural Human MIC Proteins with Internal Targeting Domains Plasmid Construction and Expression The secretion signal sequence and codons 1-276 of mature HUMMHCREP (Human MHC class I-related protein mRNA) were obtained by amplifying with a Polymerase Chain Reaction (PCR) the appropriate DNA sequence from human spleen first-strand cDNA (available from Life Technologies/Invitrogen) using primers AV1466 (SEQ. ID. NO. 30) and AV1448 (SEQ. ID. NO. 31).

The amplified DNA product was digested with NheI and HindIII restriction enzymes, and the resulting product was ligated into NheI/HindIII-digested pCDNA5/FRT (Invitrogen), to create pSW265.

The DNA of the inserted PCR product was sequenced and verified to include an NheI site followed by 26 bases of the 5'untranslated (UT) sequence, followed by secretion signal sequence and codons 1-276 of mature HUMMHCREP, followed by a termination codon, followed by a HindIII site. Where the coding sequence deviated from the intended sequence such that it would result in an amino acid difference if translated, the codons were changed by site-directed mutagenesis (using New England BioLabs Phusion® Site-Directed Mutagenesis Kit and appropriate primers) so that the amino acid sequence matched the relevant portion (amino acids 1-276) of the sequence described as SEQ. ID. NO. 13.

The corrected plasmid was designated pSW271 and contained the corrected DNA sequence encoding 26 bases of the 5'UT sequence, followed by secretion signal sequence and codons 1-276 of mature HUMMHCREP, followed by a termination codon, SEQ. ID. NO.14

Primers AV1490 (SEQ. ID. NO. 32) and AV1489 (SEQ. ID. NO. 33) and pSW271 were used to generate a PCR product which was subsequently digested with BamHI and BsmBI and ligated to ~5259 bp BamHI/BsmBI fragment from pSW271. The resulting construct pSW275 lacks a BsmBI site.

Using New England BioLabs Phusion® Site-Directed Mutagenesis Kit and primers AV1493 (SEQ. ID. NO. 34) and AV1494 (SEQ. ID. NO. 35), two BsmBI sites were inserted in the MICA coding region, creating pSW276.

The plasmid pSW276 was digested with BsmBI and ligated to kinased and annealed oligonucleotides AV1826 (SEQ. ID. NO. 36) and AV1827 (SEQ. ID. NO. 37) to create pKK35. This plasmid contained a sequence encoding SGGSGGGSHHHHHHHHHHHSGGSGGG (SEQ. ID. NO. 38) between MICA residues Isoleucine 249 and Cysteine 259 and replacing the residues at positions 250-258.

For plasmid construct pKK35 a 90% confluent culture of 293T cells (ATCC) in a 10 cm tissue culture dish was transfected with 10 µg of the plasmid using Fugene HD transfection reagent (Roche Applied Science). After 3 days the culture medium of each culture was collected and cleared of floating cells by centrifugation at 4000 rpm in an Eppendorf 5810R tabletop centrifuge. To the recovered ~9.5 ml was added 1 ml of 0.5 M sodium phosphate buffer pH 7.0, 1.5 M NaCl, 0.1 M imidazole.

Ni-NTA resin was purchased from Qiagen (catalog AV36111) and washed with 0.05 M sodium phosphate buffer pH 7.0, 0.15 M NaCl, 0.01 M imidazole. To 8 ml culture medium from each of the transfected 293T cell cultures was added 0.35 ml of the Ni-NTA resin. The samples were rocked at 25° C. for 4 hrs then centrifuged for 5 min @ 1,200 rpm in the Eppendorf 5810R tabletop centrifuge. The supernatant was removed by aspiration and discarded. The resin was washed 3 times with 10 ml wash buffer (50 mM sodium phosphate buffer pH 8.0, 300 mM NaCl, 20 mM imidazole).

After the third wash, 6 mls of elution buffer (50 mM sodium phosphate buffer pH 8.0, 300 mM NaCl, 250 mM imidazole) was added to the resin. The samples were rocked overnight at 4° C. The next day samples were centrifuged at 4000 rpm in the Eppendorf 5810R tabletop centrifuge, and the supernatants were removed new tubes.

Each sample was concentrated using a Pierce concentrator 7 ml/9K (catalog AV89884A) spin tube. The concentrators were pre-rinsed with phosphate buffered saline (PBS). Samples were added to the concentrator and then centrifuged for 30 min at 4000 rpm in the Eppendorf 5810R tabletop centrifuge. Each sample was washed and concentrated 3 times with 6 ml PBS—each time spinning 4000 rpm 30 min in the Eppendorf 5810R tabletop centrifuge.

For SDS-PAGE analyses of the proteins secreted from 293T cells transiently transfected with plasmid pKK35, the samples were mixed with equal volumes of Novex Tris-Glycine SDS 2× sample buffer (Invitrogen AVLC2676) and electrophoresed on 4-20% Tris-Glycine Gradient Gel (Invitrogen AVEC60285BOX). Identical gels were stained with Coomassie Blue to detect proteins non-specifically or western blotted using a goat polyclonal antibody detecting human MICA, FIG. 5. For western blotting the electrophoresed sample lanes in the slab gel were transferred to a nitrocellulose membrane (Invitrogen Nitrocellulose Membrane Filter Paper Sandwich AVLC2001) using an Invitrogen XCell II Blot Module (AVEI9051). The membrane filter was blocked overnight at 4° C. in 5% milk-PBST. Primary antibody (anti-human MICA antibody—R&D Systems AVAF1300) was used at 1:500 dilution in 5% milk-PBST. The resulting filter "blot" was incubated 2 hrs at 25° C. with gentle rocking The filter "blot" was subsequently washed for 20 min at 25° C. with PBST after which the secondary antibody (anti-goat IgG-HRP antibody—R&D Systems AVHAF017) was added at a dilution of 1:1000 in 5% milk-PBST. The filter "blot" was rocked for 2 hrs at 25° C. and then again was washed 20 min in PBST. The filter "blot" was developed with Novex HRP Chromogenic Substrate—TMB (Invitrogen AVWP20004).

What is claimed is:

1. A non-natural, monomeric, soluble, mammalian MHC class I chain-related (MIC) molecule comprising an α1-α2 platform domain attached to a targeting motif, wherein the α1-α2 platform domain is at least 80% identical to a native α1-α2 platform domain of a human MICA or MICB protein, and wherein the α1-α2 platform domain binds an NKG2D receptor, and wherein the targeting motif comprises a MIC α3 domain and a heterologous peptide, wherein the heterologous peptide is inserted into the MIC α3 domain at a non-carboxy-terminal site, and wherein the heterologous peptide directs the binding of the targeting motif to a target molecule on a target cell, thereby delivering the attached α1-α2 platform domain to the target cell.

2. The molecule of claim 1 wherein the α3 domain is from a human MICA or MICB protein.

3. The molecule of claim 1 wherein the α3 domain is a complete native α3 domain without a deletion.

4. The molecule of claim 1 wherein the α3 domain is a native α3 domain, wherein a portion of the domain has been deleted.

5. The molecule of claim 4, wherein the portion deleted is adjacent to the insertion site.

6. The molecule of claim 1 wherein the α3 domain comprises a deletion, insertion, amino acid substitution, mutation, or combination thereof at site different from the insertion site.

7. The molecule of claim 1 wherein the MICA protein is selected from the group consisting of SEQ ID NOs:1-6, and 13.

8. The molecule of claim 1, wherein the target molecule is a cell-surface molecule.

9. The molecule of claim 1 wherein the target cell is malignant and the target molecule is a human epidermal growth factor receptor 2 (HER2), NK-1R, Epidermal Growth Factor Receptor (EGFR), Erb2 or melanoma antigen; antigens of LNcaP and PC-3 prostate cancer cells; a growth factor receptor, an angiogenic factor receptor, an integrin, or an oncogene-encoded protein product, or a fragment thereof.

10. The molecule of claim 1 wherein the target cell is infected by a virus and the target molecule on the target cell is a phosphotidylserine, or a phosphotidylserine with an accessory protein; or a surface glycoprotein encoded by a virus, an adenovirus, a human immunodeficiency virus, a herpetic virus, a pox virus, a flavivirus, a filovirus, a hepatitis virus, a papilloma virus, cytomegalovirus, vaccinia, rotavirus, influenza, a parvo virus, West Nile virus, rabies, polyoma, rubella, distemper virus, or Japanese encephalitis virus.

11. The molecule of claim 1 wherein the heterologous peptide is a complementarity determining region of an antibody.

12. The molecule of claim 1 wherein the insertion is within or adjacent to a solvent-exposed loop of the α3 domain.

13. A composition comprising the non-natural, monomeric, MIC molecule of claim 1 and a carrier or excipient.

* * * * *

SEQUENCE LISTING

```
<160> NUMBER OF SEQ ID NOS: 41

<210> SEQ ID NO 1
<211> LENGTH: 274
<212> TYPE: PRT
<213> ORGANISM: Homo sapiens

<400> SEQUENCE: 1

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95
```

```
Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Trp Thr
            115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr Leu Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
            195                 200                 205

Pro Trp Asn Ile Thr Leu Ser Trp Arg Gln Asp Gly Val Ser Leu Ser
            210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 2
<211> LENGTH: 274
<212> TYPE: PRT
<213> ORGANISM: Homo sapiens

<400> SEQUENCE: 2

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Trp Thr
            115                 120                 125

Met Pro Gln Ser Ser Arg Ala Gln Thr Leu Ala Met Asn Ile Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
```

```
                195                 200                 205
Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 3
<211> LENGTH: 274
<212> TYPE: PRT
<213> ORGANISM: Homo sapiens

<400> SEQUENCE: 3

Glu Pro His Ser Leu Pro Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 4
<211> LENGTH: 274
```

```
<212> TYPE: PRT
<213> ORGANISM: Homo sapiens

<400> SEQUENCE: 4

Glu Pro His Ser Leu Arg Tyr Asn Leu Thr Val Leu Ser Trp Asp Gly
 1               5                  10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
         35                  40                  45

Trp Ala Glu Asp Val Leu Gly Asn Lys Thr Trp Asp Arg Glu Thr Arg
 50                  55                  60

Asp Leu Thr Gly Asn Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
             100                 105                 110

Asp Gly Glu Leu Phe Leu Ser Gln Asn Leu Glu Thr Glu Glu Trp Thr
         115                 120                 125

Val Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Glu Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 5
<211> LENGTH: 274
<212> TYPE: PRT
<213> ORGANISM: Homo sapiens

<400> SEQUENCE: 5

Glu Pro His Ser Leu Arg Tyr Asn Leu Thr Val Leu Ser Trp Asp Gly
 1               5                  10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
         35                  40                  45

Trp Ala Glu Asp Val Leu Gly Asn Lys Thr Trp Asp Arg Glu Thr Arg
 50                  55                  60

Asp Leu Thr Gly Asn Gly Lys Asp Leu Arg Met Thr Leu Ala His Ile
 65                  70                  75                  80
```

```
Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Trp Thr
            115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
            195                 200                 205

Pro Trp Asn Ile Thr Leu Ser Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
                260                 265                 270

Pro Ser

<210> SEQ ID NO 6
<211> LENGTH: 274
<212> TYPE: PRT
<213> ORGANISM: Homo sapiens

<400> SEQUENCE: 6

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Trp Thr
            115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175
```

```
Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
            195                 200                 205

Pro Trp Asn Ile Thr Leu Ser Trp Arg Gln Asp Gly Val Ser Leu Ser
            210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 7
<211> LENGTH: 305
<212> TYPE: PRT
<213> ORGANISM: Homo sapiens

<400> SEQUENCE: 7

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Lys Thr Trp Asp Thr Glu Thr Glu Asp
    50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asp
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
    130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Leu Pro Pro Met Val Asn Val Ile
                165                 170                 175

Cys Ser Glu Val Ser Glu Gly Asn Ile Thr Val Thr Cys Arg Ala Ser
            180                 185                 190

Ser Phe Tyr Pro Arg Asn Ile Thr Leu Thr Trp Arg Gln Asp Gly Val
        195                 200                 205

Ser Leu Ser His Asn Thr Gln Gln Trp Gly Asp Val Leu Pro Asp Gly
    210                 215                 220

Asn Gly Thr Tyr Gln Thr Trp Val Ala Thr Arg Ile Arg Gln Gly Glu
225                 230                 235                 240

Glu Gln Arg Phe Thr Cys Tyr Met Glu His Ser Gly Asn His Gly Thr
                245                 250                 255

His Pro Val Pro Ser Gly Lys Ala Leu Val Leu Gln Ser Gln Arg Thr
            260                 265                 270

Asp Phe Pro Tyr Val Ser Ala Ala Met Pro Cys Phe Val Ile Ile Ile
```

```
                      275                 280                 285
Ile Leu Cys Val Pro Cys Cys Lys Lys Thr Ser Ala Ala Glu Gly
            290                 295                 300

Pro
305

<210> SEQ ID NO 8
<211> LENGTH: 317
<212> TYPE: PRT
<213> ORGANISM: Homo sapiens

<400> SEQUENCE: 8

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Glu Thr Trp Asp Thr Glu Thr Glu Asp
    50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Met His Glu Asp Ser Ser Thr Arg Gly Ser Arg His Phe Tyr Tyr Asn
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
    130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
        195                 200                 205

Arg Asn Ile Thr Leu Thr Trp Arg Gln Asp Gly Val Ser Leu Ser His
    210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
                245                 250                 255

Thr Cys Tyr Met Glu His Ser Gly Asn His Gly Thr His Pro Val Pro
            260                 265                 270

Ser Gly Lys Ala Leu Val Leu Gln Ser Gln Arg Thr Asp Phe Pro Tyr
        275                 280                 285

Val Ser Ala Ala Met Pro Cys Phe Val Ile Ile Ile Leu Cys Val
    290                 295                 300

Pro Cys Cys Lys Lys Thr Ser Ala Ala Glu Gly Pro
305                 310                 315

<210> SEQ ID NO 9
<211> LENGTH: 317
<212> TYPE: PRT
```

<213> ORGANISM: Homo sapiens

<400> SEQUENCE: 9

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Lys Thr Trp Asp Thr Glu Thr Glu Asp
    50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asp
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
    130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Ile Cys Ser Glu Val
            180                 185                 190

Ser Glu Gly Asn Ile Thr Val Thr Cys Arg Ala Ser Ser Phe Tyr Pro
        195                 200                 205

Arg Asn Ile Thr Leu Thr Trp Arg Gln Asp Gly Val Ser Leu Ser His
    210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
                245                 250                 255

Thr Cys Tyr Met Glu His Ser Gly Asn His Gly Thr His Pro Val Pro
            260                 265                 270

Ser Gly Lys Ala Leu Val Leu Gln Ser Gln Arg Thr Asp Phe Pro Tyr
        275                 280                 285

Val Ser Ala Ala Met Pro Cys Phe Val Ile Ile Ile Leu Cys Val
    290                 295                 300

Pro Cys Cys Lys Lys Thr Ser Ala Ala Glu Gly Pro
305                 310                 315

<210> SEQ ID NO 10
<211> LENGTH: 317
<212> TYPE: PRT
<213> ORGANISM: Homo sapiens

<400> SEQUENCE: 10

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

```
Ala Glu Asn Val Leu Gly Ala Lys Thr Trp Asp Thr Glu Thr Glu Asp
         50                  55                  60

Leu Thr Glu Asn Gly Gln Asp Leu Arg Arg Thr Leu Thr His Ile Lys
 65                  70                  75                  80

Asp Gln Lys Gly Gly Leu His Ser Leu Gln Glu Ile Arg Val Cys Glu
                 85                  90                  95

Ile His Glu Asp Ser Ser Thr Arg Gly Ser Arg His Phe Tyr Tyr Asp
             100                 105                 110

Gly Glu Leu Phe Leu Ser Gln Asn Leu Glu Thr Gln Glu Ser Thr Val
         115                 120                 125

Pro Gln Ser Ser Arg Ala Gln Thr Leu Ala Met Asn Val Thr Asn Phe
130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
        195                 200                 205

Arg Asn Ile Thr Leu Thr Trp Arg Gln Asp Gly Val Ser Leu Ser His
210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
                245                 250                 255

Thr Cys Tyr Met Glu His Ser Gly Asn His Gly Thr His Pro Val Pro
            260                 265                 270

Ser Gly Lys Ala Leu Val Leu Gln Ser Gln Arg Thr Asp Phe Pro Tyr
        275                 280                 285

Val Ser Ala Ala Met Pro Cys Phe Val Ile Ile Ile Leu Cys Val
290                 295                 300

Pro Cys Cys Lys Lys Lys Thr Ser Ala Ala Glu Gly Pro
305                 310                 315

<210> SEQ ID NO 11
<211> LENGTH: 317
<212> TYPE: PRT
<213> ORGANISM: Homo sapiens

<400> SEQUENCE: 11

Pro His Ser Leu Arg Tyr Asn Leu Met Val Leu Ser Gln Asp Gly Ser
  1               5                  10                  15

Val Gln Ser Gly Phe Leu Ala Glu Gly His Leu Asp Gly Gln Pro Phe
             20                  25                  30

Leu Arg Tyr Asp Arg Gln Lys Arg Arg Ala Lys Pro Gln Gly Gln Trp
         35                  40                  45

Ala Glu Asp Val Leu Gly Ala Glu Thr Trp Asp Thr Glu Thr Glu Asp
     50                  55                  60

Leu Thr Glu Asn Gly Gln Asp Leu Arg Arg Thr Leu Thr His Ile Lys
 65                  70                  75                  80

Asp Gln Lys Gly Gly Leu His Ser Leu Gln Glu Ile Arg Val Cys Glu
                 85                  90                  95

Ile His Glu Asp Ser Ser Thr Arg Gly Ser Arg His Phe Tyr Tyr Asn
            100                 105                 110
```

```
Gly Glu Leu Phe Leu Ser Gln Asn Leu Glu Thr Gln Glu Ser Thr Val
            115                 120                 125

Pro Gln Ser Ser Arg Ala Gln Thr Leu Ala Met Asn Val Thr Asn Phe
130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
            165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
            195                 200                 205

Arg Asn Ile Thr Leu Thr Trp Arg Gln Asp Gly Val Ser Leu Ser His
            210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Lys Phe
            245                 250                 255

Thr Cys Tyr Met Glu His Ser Gly Asn His Gly Thr His Pro Val Pro
            260                 265                 270

Ser Gly Lys Ala Leu Val Leu Gln Ser Gln Arg Thr Asp Phe Pro Tyr
            275                 280                 285

Val Ser Ala Ala Met Pro Cys Phe Val Ile Ile Ile Leu Cys Val
            290                 295                 300

Pro Cys Cys Lys Lys Lys Thr Ser Ala Ala Glu Gly Pro
305                 310                 315

<210> SEQ ID NO 12
<211> LENGTH: 317
<212> TYPE: PRT
<213> ORGANISM: Homo sapiens

<400> SEQUENCE: 12

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Glu Thr Trp Asp Thr Glu Thr Glu Asp
50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asn
            100                 105                 110

Gly Glu Leu Phe Leu Ser Gln Asn Leu Glu Thr Gln Glu Ser Thr Val
            115                 120                 125

Pro Gln Ser Ser Arg Ala Gln Thr Leu Ala Met Asn Val Thr Asn Phe
130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
            165                 170                 175
```

```
Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
        195                 200                 205

Arg Asn Ile Thr Leu Thr Trp Arg Gln Asp Gly Val Ser Leu Ser His
    210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
                245                 250                 255

Thr Cys Tyr Met Glu His Ser Gly Asn His Gly Thr His Pro Val Pro
            260                 265                 270

Ser Gly Lys Ala Leu Val Leu Gln Ser Gln Arg Thr Asp Phe Pro Tyr
        275                 280                 285

Val Ser Ala Ala Met Pro Cys Phe Val Ile Ile Ile Leu Cys Val
    290                 295                 300

Pro Cys Cys Lys Lys Lys Thr Ser Ala Ala Glu Gly Pro
305                 310                 315

<210> SEQ ID NO 13
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220
```

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
            245                 250                 255

Phe Thr Cys Tyr Met Glu His Ser Gly Asn His Ser Thr His Pro Val
        260                 265                 270

Pro Ser Gly Lys
        275

<210> SEQ ID NO 14
<211> LENGTH: 937
<212> TYPE: DNA
<213> ORGANISM: Homo sapiens

<400> SEQUENCE: 14
gctagcgctg agagggtggc gacgtcgggg ccatggggct gggcccggtc ttcctgcttc    60
tggctggcat cttcccttt gcacctccgg gagctgctgc tgagcccac agtcttcgtt    120 ataacctcac ggtgctgtcc tgggatggat ctgtgcagtc agggtttctc actgaggtac   180
atctggatgg tcagcccttc ctgcgctgtg acaggcagaa atgcagggca agccccagg    240 gacagtgggc agaagatgtc ctgggaaata agacatggga cagagagacc agggacttga   300
cagggaacgg aaaggacctc aggatgaccc tggctcatat caaggaccag aaagaaggct   360
tgcattccct ccaggagatt agggtctgtg agatccatga agacaacagc accaggagct   420
cccagcattt ctactacgat ggggagctct tcctctccca aacctggaga ctaaggaatg   480
gacaatgccc cagtcctcca gagctcagac cttggccatg aacgtcagga atttcttgaa   540
ggaagatgcc atgaagacca agacacacta tcacgctatg catgcagact gcctgcagga   600
actacggcga tatctaaaat ccggcgtagt cctgaggaga acagtgcccc ccatggtgaa   660
tgtcacccgc agcgaggcct cagagggcaa cattaccgtg acatgcaggg cttctggctt   720
ctatccctgg aatatcacac tgagctggcg tcaggatggg gtatctttga gccacgacac   780
ccagcagtgg ggggatgtcc tgcctgatgg gaatggaacc taccagacct gggtggccac   840
caggatttgc caaggagagg agcagaggtt cacctgctac atggaacaca gcgggaatca   900
cagcactcac cctgtgccct ctgggaaata aaagctt                            937

<210> SEQ ID NO 15
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tatgaaatac ctgctgccga ccgctgctgc tggtctgctg ctcctcgctg cccagcc       57

<210> SEQ ID NO 16
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
catgggctgg gcagcgagga gcagcagacc agcagcagcg tcggcagca ggtatttca     59

-continued

```
<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
catgcatcat caccatcacc acctcgagga attcaagctt ggatccgc                48

<210> SEQ ID NO 18
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcagcggatc caagcttgaa ttcctcgagg tggtgatggt gatgatg                 47

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19 tttttttgcta gcgctgagag ggtggcgacg tc                                32

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctttccaagc ttttatttcc cagagggcac agggtg                             36

<210> SEQ ID NO 21
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tccctcctcg aggaaaactt gtactttcaa ggcgagcccc acagtcttcg ttataacc     58

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22 cccccggat ccatgattac tcatggttgt tatacccg                            38

<210> SEQ ID NO 23
<211> LENGTH: 34
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23 cccccccaagc ttattctaca caaaccgcat agac                                   34

<210> SEQ ID NO 24
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24 tttttttctcg aggtggtgat ggtgatgatg tcggccttca ataccgccgc tggccttggt       60
ttgatc                                                                   66

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25 ccccccccata tgattactca tggttgttat acccgg                                 36

<210> SEQ ID NO 26
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aaaaaactcg aggaaaactt gtactttcaa ggcacagtgc cacccatggt gaatgtcacc       60
cgcag                                                                    65

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atatataagc ttttatttcc cagagggcac                                         30

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttttttcgtc tctcatgatt actcatggt                                          29
```

<210> SEQ ID NO 29
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
atatacatac agtcgaccag gttgggggcg gtattgaagg ccgacatc                48

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 30 tttttttgcta gcgctgagag ggtggcgacg tc                                32

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ctttccaagc ttttatttcc cagagggcac agggtg                             36

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
aatcacagca ctcaccctgt gccc                                          24

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
tcccttcgtc tctggtcgga tacgctgtcg aactttcga tc                       42

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
gaatcctggt ggccacccag gtctgg                                        26

<210> SEQ ID NO 35
<211> LENGTH: 43

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gagacgacaa acgtctcttg ctacatggaa cacagcggga atc                        43

<210> SEQ ID NO 36
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gattagtggt ggcagtggcg gcggtagtca tcatcaccac catcaccacc atcaccacag      60
cggcggcagc ggtggcggt                                                   79

<210> SEQ ID NO 37
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agcaaccgcc accgctgccg ccgctgtggt gatggtggtg atggtggtga tgatgactac      60
cgccgccact gccaccact                                                   79

<210> SEQ ID NO 38
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Gly Gly Ser Gly Gly Gly Ser His His His His His His His
1               5                  10                  15

His His Ser Gly Gly Ser Gly Gly Gly
            20                  25

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis

<400> SEQUENCE: 39

His His His His His His
1               5

<210> SEQ ID NO 40
<211> LENGTH: 7
<212> TYPE: PRT
<213> ORGANISM: Unknown
<220> FEATURE:
<223> OTHER INFORMATION: Description of Unknown: Tev protease
      cleavage site peptide
```

-continued

```
<400> SEQUENCE: 40

Glu Asn Leu Tyr Phe Gln Gly
1               5

<210> SEQ ID NO 41
<211> LENGTH: 4
<212> TYPE: PRT
<213> ORGANISM: Unknown
<220> FEATURE:
<223> OTHER INFORMATION: Description of Unknown: Factor Xa
      cleavage site peptide

<400> SEQUENCE: 41

Ile Glu Gly Arg
1
```